United States Patent [19]

Glassman

[11] Patent Number: 4,711,236
[45] Date of Patent: Dec. 8, 1987

[54] SURGICAL DRAPE

[76] Inventor: Jacob A. Glassman, 1680 Michigan Ave., Miami Beach, Fla. 33139

[21] Appl. No.: 698,162

[22] Filed: Feb. 25, 1985

Related U.S. Application Data

[63] Continuation-in-part of Ser. No. 395,803, Jul. 6, 1982, Pat. No. 4,524,767.

[51] Int. Cl.⁴ ............................................. A61F 13/00
[52] U.S. Cl. ................................................ 128/132 D
[58] Field of Search .............. 128/132 R, 132 D, 156, 128/165, 155

[56] References Cited

U.S. PATENT DOCUMENTS

| | | | |
|---|---|---|---|
| 3,060,932 | 10/1982 | Pereny et al. .................. | 128/132 D |
| 3,721,234 | 3/1973 | Hadtke et al. .................. | 128/132 D |
| 3,930,497 | 1/1976 | Krebs et al. ..................... | 128/132 D |
| 4,196,723 | 4/1980 | Moose, Jr. ....................... | 128/132 D |
| 4,253,451 | 3/1981 | Soloman .......................... | 128/132 D |
| 4,413,621 | 11/1983 | McCracken et al. ........... | 128/155 X |
| 4,485,809 | 12/1984 | Dellas ................................ | 128/156 |

Primary Examiner—Robert A. Hafer
Assistant Examiner—Kathleen J. D'Arrigo
Attorney, Agent, or Firm—Elmer L. Zwickel

[57] ABSTRACT

A surgical drape including an abdominal drape of the thoracic type designed for limb surgery and/or amputation procedures having a plurality of absorbent flaps strategically arranged around the fenstration and situated below an incise drape that is wrapped around and adhered to the skin of the critical area of the limb.

6 Claims, 6 Drawing Figures

FIG. 1
FIG. 2
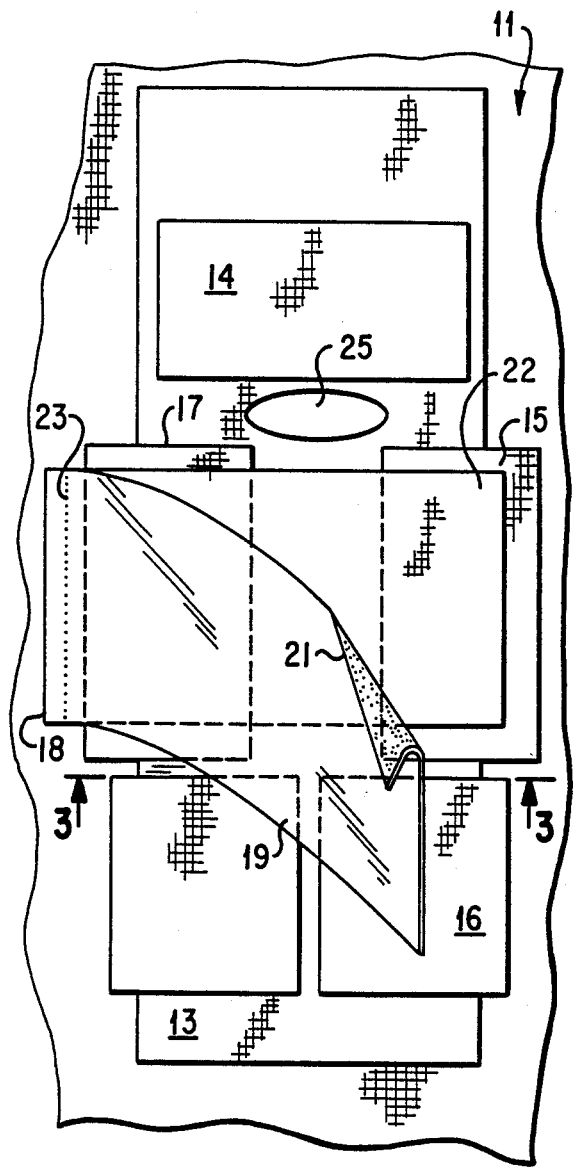
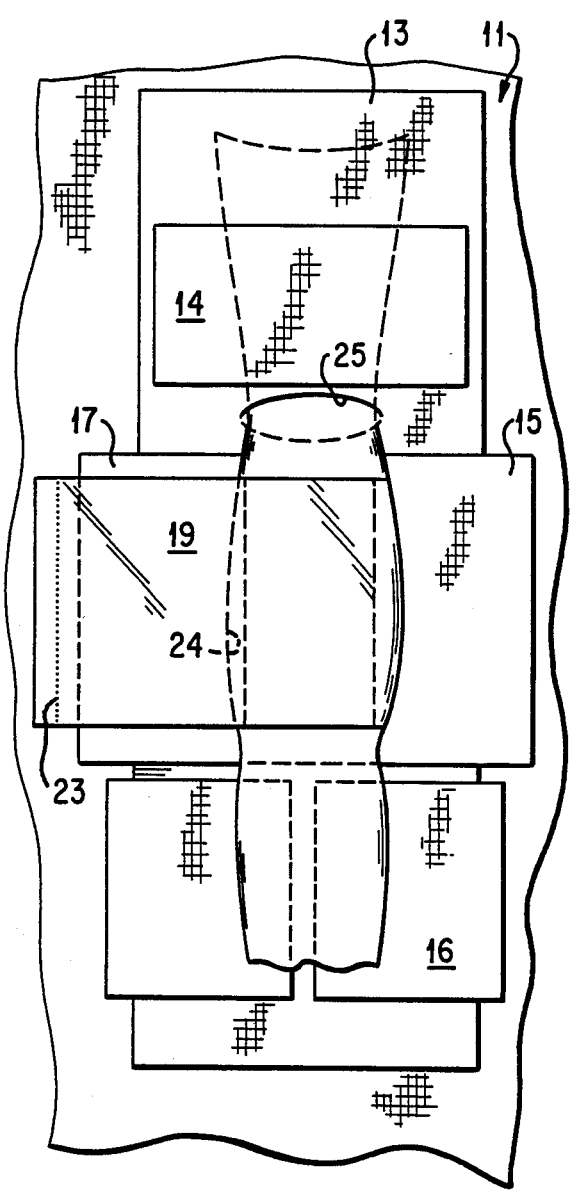
FIG. 3
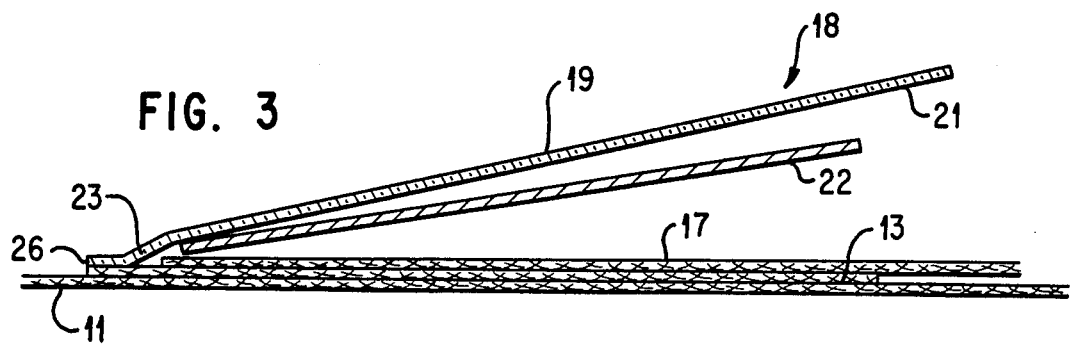

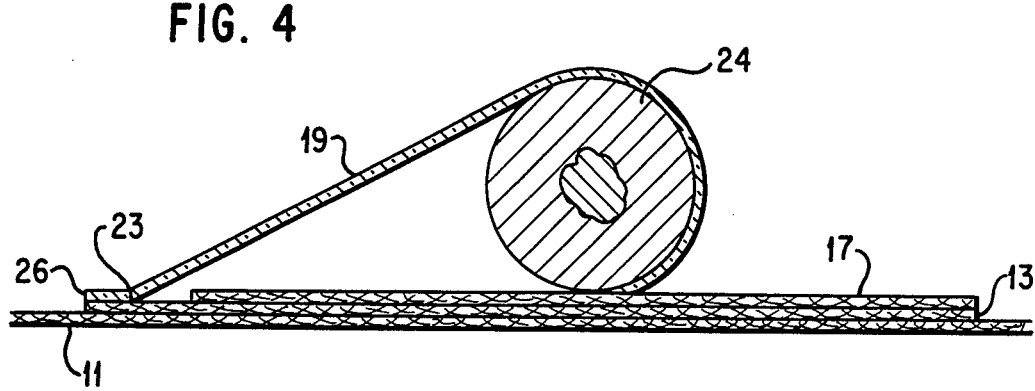
FIG. 4
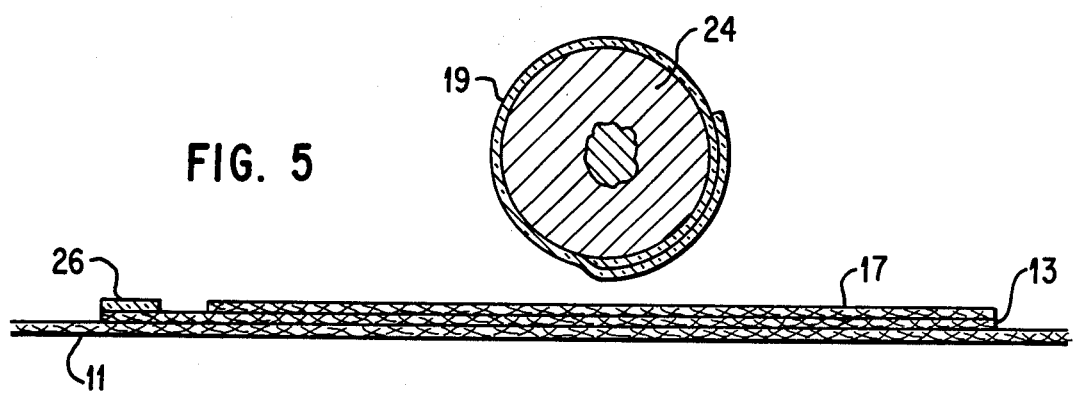
FIG. 5
FIG. 6
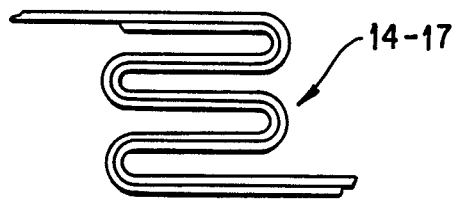

SURGICAL DRAPE

This application is a continuation-in-part of applicant's U.S. application Ser. No. 395,802, entitled Surgical Drapes, filed July 6, 1982, in Art Unit 335, allowed on Oct. 14, 1984, and now U.S. Pat. No. 4,524,767.

The invention relates to improvements in surgical drapes and particularly to an abdominal and thoracic type of incise drape especially designed for limb surgery and also for amputation procedures. Generally, most surgical drapes are fabricated from non-woven absorbent and non-absorbent disposable material shaped and sized to adapt them to various surgical needs. They include operative openings of various size and shape affording access by the surgeon to the underlying skin. Specifically, the herein disclosed surgical drape preferably employs a transverse opening or slot through which the patient's entire limb to be operated on is passed through. Now, assuming that the operation to be performed is to be on the patient's thigh; then the foot, leg and knee, which are now lying on top of the surgical drape are first sterilized and then sterilly wrapped so as to be excluded from the operative field, leaving only the thigh exposed for surgery.

The structure of the drape herein disclosed, is comprised of a regular non-woven surgical or main drape having an opening through which the limb (such as the leg illustrated) is passed. After the foot, leg and knee are wrapped as aforesaid, the thigh is wrapped or encircled in a transparent incise type of drape. This incise drape is initially adhesively adheared to the surgical drape at one site but readily separates therefrom prior to beginning the surgery so as to allow for free maneuverability of the thigh which is necessary for successful surgery.

It is an object of the invention to provide a surgical drape especially designed for limb surgery wherein the limb or a select portion thereof, can be sterilely sealed before surgery is started.

Another object of the invention is to provide a surgical drape of a character that includes novel means to restrain movement of the subject limb during the process of enclosing said limb in the drape prior to the proposed surgery.

Another object is to provide novel means whereby the restrained limb may be quickly freed from it's restraining means.

Another object is to provide a surgical drape that is convenient for the surgeon to use and is not difficult to use nor expensive to produce.

The structure by means of which the above noted and other advantages of the invention are attained will be described in the following specification, taken in conjunction with the accomanying drawings, showing a preferred illustrative embodiments of the invention, in which:

FIG. 1 is a plan view of a main drape combination of a character most generally utilized for limb surgery.

FIG. 2 illustrates the drape assembly associated with a limb to be operated upon or amputated, prior to total sterile coverage and which also shows the detachable fixation of the four absorbent towels arranged around the periphery of the fenestration.

FIG. 3 is a longitudinal section, on an enlarged scale of the "Vi-DRAPE" (Trade mark of Minnesota, Mining & Manufacturing Co) layers partially separated just prior to use, taken substantially on line 3—3 of FIG. 1.

FIG. 4 is a similar sectional view showing the V-i-draperpartially wrapped around the subject thigh.

FIG. 5 is a view similar to FIG. 4, showing the Vi-drape wrapped totally around the thigh and adhesively secured thereto, and the thigh being released from attachment to the main drape.

FIG. 6 is an elevational view of the toweling when furnished in folded form as distinguished from being rolled or flate.

Now, referring to the embodiment of the invention disclosed in the accompanying drawings, the abdominal and thoracic type of surgical drape 11 illustrated, is especially designed for use when operating on a patient's limb 12 or when amputating all or a portion of same. As illustrated, the main abdominal drape 11, which may comprise a relatively large base sheet 13 of non-woven absorbent or non-absorbent material, either transparent or translucent, and of sufficient size to be arranged in such manner as to underlie the patient's limb 12. Located on the top surface of the base sheet 13, beneath limb 12, are four strategically placed towels 14, 15, 16 and 17.

Upon this assembly of the surgical drape base element 13 and toweling 14–17 thereon, there is arranged a sterile incise drape 18 comprised of a top "Vi-DRAPE" sheet 19 which is adhesively coated on its bottom surface, as at 21, and adhesively joined to the removable protective sheet 22. In use, the incise drape 18 is elevated along its perforated hinge line 23 whereupon the protective sheet 22 is withdrawn from beneath it so that the adhesive bearing top sheet may be carried down over the patient's thigh 24 and partially adhered thereto initially as shown in FIG. 4. A marginal flap 23a at one end of the top sheet 19 is secured to the base drape. When the incise drape 18 is to be employed, the lower protective layer of sheet 22 is peeled off the bottom face of top sheet 19 as illustrated in FIG. 3, thus exposing the adhesive covered bottom surface of the "Vi-drape" sheet 19.

The drape assembly, comprising surgical drape 11 and base sheet 13, each have an aligned transverse opening 25 located just above the upper edge of the incise drape 18 through both of which the entire limb 12 is projected. The limb 12 is thus carried into a position above drapes 11-13 and beneath the combined sheets 19-22. The bottom sheet is removed from the adhesive coated face of sheet 19 and the "Vi-drape" sheet 19 may then be laid over and secured to the thigh 24, as best shown in FIG. 4.

Following this, the transparent "Vi-drape" sheet is separated from the base drape 11 whereupon the sheet 19 may be wrapped around the thigh to completely enclose same. Thus the thigh is sealed by the "Vi-drape" against germ activity and may be incised as required. Any free flowing fluids engendered by the incise, are absorbed by the toweling 14–17 which may be folded, as shown in FIG. 6, or otherwise gathered to wall off the operative site.

In practice, the bottom sheet 22 is peeled off the top protective sheet 19 and sheet 19 is then partially wrapped around and adhesively secured to the thigh, as shown in FIG. 4. Because the sheet 19 is initially attached to the main drape 11, by an end flap 26 (FIG. 4) to hold the incise drape 18 in place, said connection is now severed by tearing or cutting sheet 19 off at the perforation hinge line 23 so that the thigh 24 can be completely wrapped therein. Thus the thigh becomes totally free of the main drape and may be moved about into various positions to any extent necessary to perform the required surgery.

Although I have described a preferred embodiment of the invention in considerable detail, it will be understood that the description thereof is intended to be illustrative rather than restrictive as many details of the structure may be modified or changed without departing from the spirit or scope of the invention. Accordingly, I do not desire to be restricted to the exact construction shown and described.

I claim:

1. A surgical drape comprising a main drape and at least one absorbent sheet overlying and secured to said main drape, a common opening extending through the main drape and said absorbent sheet to receive a human limb extended therethrough whereby an operable portion of said limb lies over the absorbent sheet, a plurality of sheets of liquid-absorbent toweling secured to the absorbent sheet and surrounding said opening, a sterile incise drape comprising a transparent bacteriocidal top sheet, an adhesive coating on the under surface of the top sheet, a protective bottom sheet adhesively joined to the top sheet face-to-face, a detachable flap on one edge of the top sheet adapting said incise drape to be secured to any site on the main drape, said top and bottom sheets of said incise drape being separable to expose the adhesive on it's under surface, and a line of perforations dividing said transparent top sheet from the attached flap to permit complete separation of the transparent top sheet from the said flap, whereupon the freed sterile incise top sheet may be wrapped around and adhesively secured to the operable portion of the limb to completely and sterily enclose said operable portion.

2. The surgical drape recited in claim 1, wherein said incise drape and said end flap are separable along a weakened line.

3. A surgical drape comprising a main drape and at least one absorbent sheet overlying and secured to said main drape, a common opening extending through the main drape and said absorbent sheet adapted to receive a human limb extended therethrough whereby an operable portion of said limb lies over the absorbent sheet, a plurality of sheets of liquid-absorbent toweling secured to the absorbent sheet and surrounding said opening, a sterile incise drape comprising a transparent bacteriocidal top sheet, an adhesive coating on the under surface of the top sheet, a protective bottom sheet adhesively joined to the top sheet face-to-face, a flap on one edge of the top sheet adapting said incise drape to be secured to a selected site on the main drape, said top and bottom sheets of said incise drape being separable to expose the adhesive on the under surface of the top sheet and a line of perforations dividing said transparent top sheet from said flap, whereupon the freed sterile incise top sheet may be wrapped around and adhesively secured to the operable portion of the limb to completely and sterily enclose said operable portion.

4. A surgical drape comprising a main drape and at least one absorbent sheet overlying and secured to said main drape, a common opening extending through the main drape and said absorbent sheet adapted to receive a human limb extended therethrough whereby an operable portion of said limb lies over the absorbent sheet, a plurality of sheets of liquid-absorbent toweling secured to the absorbent sheet and surrounding said opening, a sterile incise drape comprising a transparent bacteriocidal top sheet, an adhesive coating on the under surface of the top sheet, a pprotective bottom sheet adhesively joined to the top sheet face-to-face, a flap on one edge of the top sheet adapting said incise drape to be secured to a selected site on the main drape, said top and bottom sheets of said incise drape being separable to expose the adhesive on it's under surface, and a weakened area separating the transparent top sheet from said flap, whereupon the sterile incise top sheet may be separated from the flap and wrapped around and adhesively secured to the operable portion of the limb to completely and sterily enclose said operable portion.

5. A surgical drape intended for use in limb surgery comprising a main drape overlying the patients body and having an opening through which the limb is adapted to be passed to locate it's operable portion on top of the main drape, an incise drape overlying the main drape including a sterile sheet to be wrapped around the surgical area of the limb, an adhesive on the bottom surface of said sterile sheet to secure the sheet to the limb, separable means securing said sterile sheet to the main drape prior to it's adhesion to the limb, means to separate said sterile sheet from the main drape to facilitate free movement of the limb after said sheet is adhesively secured thereto, and a plurality of absorbent sheets underlying the limb and surrounding the opening in the main drape, said absorbent sheets being detachably secured to the main drape a short distance away from the edges of the main drape opening.

6. The surgical drape recited in claim 5 wherein the absorbent sheets may be detached from the main drape and gathered to effectively wall off the exact operative site.

* * * * *